(12) United States Patent
Momich et al.

(10) Patent No.: US 6,335,907 B1
(45) Date of Patent: Jan. 1, 2002

(54) PACKAGE WITH INTEGRATED CIRCUIT CHIP EMBEDDED THEREIN AND SYSTEM FOR USING SAME

(76) Inventors: Robert Momich, 1123 - 95 Barlake Avenue, Hamilton, Ontario (CA), L8E 1H1; Michael E. Infuso, 1190 Royal York Road, Apartment 1, Toronto, Ontario (CA), M9A 4B3

( * ) Notice: Subject to any disclaimer, the term of this patent is extended or adjusted under 35 U.S.C. 154(b) by 0 days.

(21) Appl. No.: 09/359,322

(22) Filed: Jul. 23, 1999

(51) Int. Cl.$^7$ .............................................. G04B 47/00
(52) U.S. Cl. .............................. 368/10; 221/2; 221/15; 340/309.4
(58) Field of Search ............................. 368/10, 73, 250; 221/2, 3, 15; 340/309.15, 309.4; 600/300

(56) References Cited

U.S. PATENT DOCUMENTS

| | | |
|---|---|---|
| 4,504,153 A | 3/1985 | Schollmeyer et al. |
| 4,616,316 A | 10/1986 | Hampeter et al. |
| 4,617,557 A | 10/1986 | Gordon |
| 4,682,299 A | 7/1987 | McIntosh et al. |
| 4,725,997 A | 2/1988 | Urquhart et al. |
| 4,831,562 A | 5/1989 | McIntosh et al. |
| 4,970,669 A | 11/1990 | McIntosh et al. |
| 5,099,463 A | 3/1992 | Lloyd et al. |
| 5,181,189 A | 1/1993 | Hafner |
| 5,495,961 A | 3/1996 | Maestre |
| 5,691,932 A * | 11/1997 | Reiner et al. .................. 368/10 |
| 5,802,015 A | 9/1998 | Rothschild et al. |
| 5,805,051 A | 9/1998 | Hermann et al. |
| 5,812,064 A | 9/1998 | Barbour |
| 5,963,136 A | 10/1999 | O'Brien |
| 6,018,289 A * | 1/2000 | Sekura et al. ............ 340/309.4 |
| 6,102,855 A * | 8/2000 | Kehr et al. .................. 600/300 |

* cited by examiner

*Primary Examiner*—Vit Miska
(74) *Attorney, Agent, or Firm*—Hill & Schumacher

(57) ABSTRACT

An interactive reminder device includes a read/write module, an integrated circuit, a power supply, memory, a clock and a prompt. The read/write module is adapted to read information stored on an identifiable integrated circuit chip and to write information onto the identifiable integrated circuit chip attached to a package. The integrated circuit is operably connected to the read/write module. The power supply is operably connected to the integrated circuit. The memory is operably connected to the integrated circuit. The clock operably connected to the integrated circuit and the prompt is operably connected to the integrated circuit. The interactive reminder device is for use with a package having an integrated circuit chip attached thereto. The interactive reminder device is for implementing a system for prompting for the use of medication. The prompting system includes the steps of reading information stored on an integrated circuit chip regarding a method of calculating a next take time; calculating the next take time; storing a next take time in a prompting device; and prompting at the next take time. The prompting system may also be adapted for use in a health care facility wherein the steps include calculating the next take time for an identifiable patient for an identifiable medication; storing a next take time, the identified medication and the identified patient in a prompting device; prompting at the next take time; confirming that the medication integrated circuit chip is the medication integrated circuit chip associated with the identified medication; and confirming that the patient integrated circuit chip is the patient integrated circuit chip associated with the identified patient and thereafter administering the identified medication to the identified patient.

24 Claims, 14 Drawing Sheets

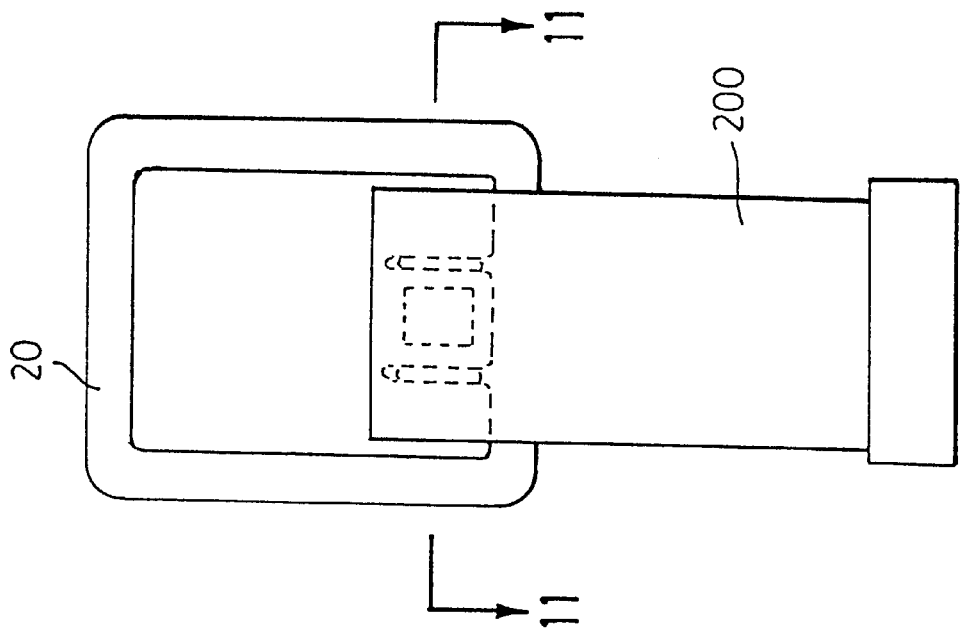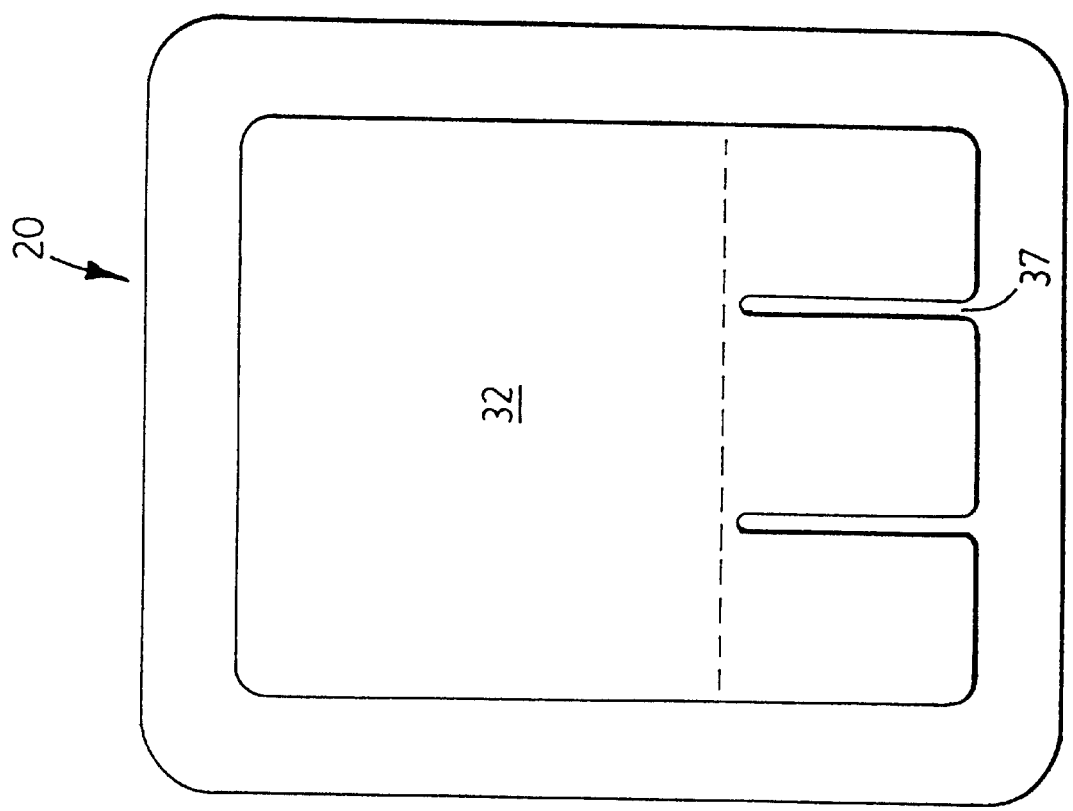

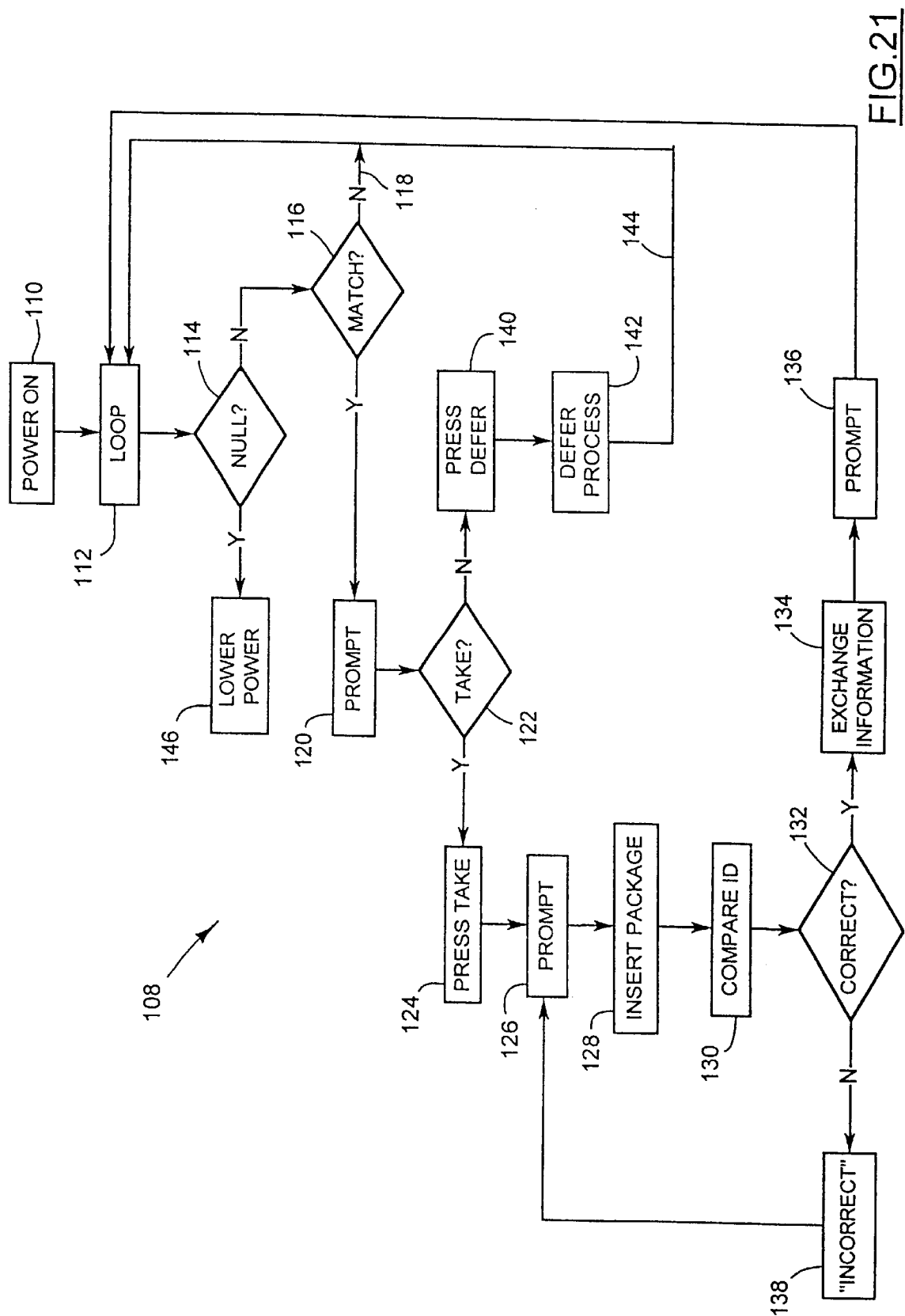

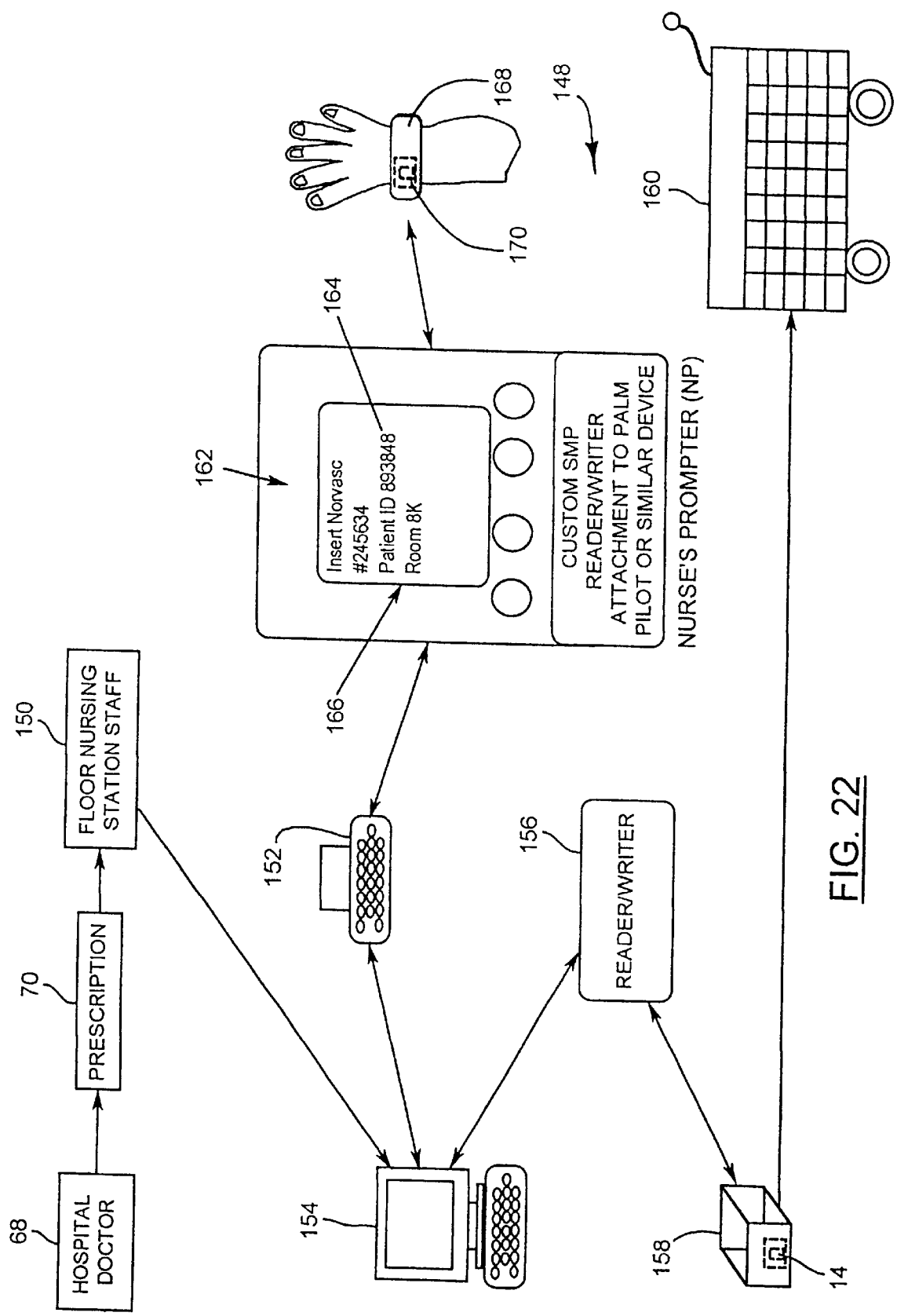

PACKAGE WITH INTEGRATED CIRCUIT CHIP EMBEDDED THEREIN AND SYSTEM FOR USING SAME

FIELD OF THE INVENTION

This invention relates to packages having attached thereto an integrated circuit chip for storing information related to the package or its contents and in particular a package having an integrated circuit chip embedded therein for interactive storage of information with regard to the contents and use over time of the package which is of particular importance in relation to the pharmaceutical Industry.

BACKGROUND OF THE INVENTION

The correct administration of medications whether by an individual or a health care professional is growing concern. In particular it is a concern where the individual takes multiple medications. Further, it is a concern as the individual gets older to ensure that he/she is taking their medication as prescribed. It is also a concern to ensure that the individual gives each health care professional a full history of medications as well as related problems.

Typically when a physician prescribes a particular medication, the physician has very little control over whether the patient actually takes the medication as prescribed. Rather, the physician must rely on the patient to take the medication as prescribed. The risk of a patient taking their medication incorrectly is increased with the number of medications. Studies have shown that in the United States the hospitalization of patients due to the incorrect administration of prescriptions drugs has increased in recent years. In some instances the incorrect use of the drug is fatal. Other studies have shown that 60% of women on the birth control pill have forgotten to take the pill everyday and as few as 20% of women actually take the pill at the same time everyday as prescribed. The result of this is that most unplanned pregnancies occur because women do not take their birth control pill regularly. One way the government is trying to address this issue is to require more comprehensive information on the drug labels. However, more effective labelling is only a partial solution since people will still forget to take the medication either at all or at the correct time.

There are concerns related to the administration of medication that need to be considered. For example some concerns are: how to ensure that the individual does not forget to take the medication at the prescribed times or at the prescribed intervals; how to ensure that the individual takes neither too few nor too many medications, and how to ensure that the individual takes the right medication or that they heed the warnings or other contra-indicators associated with the medication. In addition, it would be advantageous if the physician had a mechanism to confirm when in fact the medications were taken. This is of particular importance when the physician is trying to make minor adjustments to the medication.

In addition to these concerns, when the medication is administered by a health care professional In a hospital or other institution there are other concerns that need to be considered. For example other concerns are: how to ensure there is continuity with multiple staff for one individual, how to ensure that the medication is administered to the right individual; and how to ensure that there is a complete log of all of the medications given to a specific individual.

A number of devices have been suggested to try to address at least some of these problems. For example, a number of devices are used as reminder units for specific medications containers. For example U.S. Pat. No. 4,616,316 issued to Hanpeter et al. shows a monitoring device attached to a blister pack having conductive traces thereon such that when a trace is broken the monitoring device records the time thereof. The monitoring device includes a power source. U.S. Pat. No. 5,181,189 issued Jan. 19, 1993 to Hafner shows a signalling device that is adapted to be attached to an individual medication. The device signals when the medication is to be taken but it does not record if it has been taken. U.S. Pat. No. 5,495,961 issued Mar. 5, 1996 to Maestre shows a programmable medication alarm device designed to be attached to a medicine bottle or dispenser. Similarly, U.S. Pat. No. 4,504,153 issued Mar. 12, 1985 to Schollmeyer et al. shows a prompting device that is attached to an individual medication container. The Scholimeyer device may record when the cap was opened. There are a number of shortcomings with regard to these devices. In particular, all of these devices include a power source with the device and therefore with the medication and accordingly these devices would be expensive to operate. Further, these devices do not have a method of providing contra-indications or handling multiple medications.

Alternatively, more comprehensive devices have been suggested. For example U.S. Pat. No. 4,831,562 issued May 16, 1989 to McIntosh et al. shows a reminder device that includes individual compartments for each different medication. The device is programmed to provide a reminder signal and provide a display to indicate that a medication should be taken. Similarly U.S. Pat. No. 5,805,061 issued Sep. 8, 1998 to Hermann et al. shows an interactive medication reminder/dispenser device with a plurality of compartments for different medications. The device provides a visual and audio signal indicative of a time to take at (east one medication. This device may also include a weighing mechanism or an optical system which enables the device to determine if a pill has actually been removed. Alternatively the user presses a key to indicate that the medication has been taken. Both devices could also include information with regard to medication incompatibilities. Each of these devices has a power source attached thereto. There are a number of shortcomings with regard to these devices. In particular by emptying the medication into another container the user risks confusing the medication by inadvertently putting it into the wrong compartment. Further, information from the medications is read into the device but no Information with regard to the use of the medication is written back to the medication container. Therefore, no information with regard to use of the medication is attached to the medication container.

Other devices have been suggested which have specific functions with regard to the safe use of medications. For example U.S. Pat. No. 5,812,064 issued Sep. 22, 1998 to Barbour shows a device that has a medicine bottle with a memory unit attached thereto. However, the memory unit allows only for information to be transferred from the memory unit to a playback unit. No information is written from the playback unit to the memory unit. Therefore, no information with regard to actual use of the medication is carried in the memory unit. Other devices are used to indicate when the product has passed its expiration date. This can be very important with regard to medicines because after that date they may not have any value or they may become toxic. An example of such a device is U.S. Pat. No. 5,802,015 issued Sep. 1, 1998 to Rothchild et al. which shows an electronic label that indicates the expiration of a predetermined time period.

None of the prior art systems described above show a package with an interactive memory unit that both stores information with regard to the medication and the use of the medication by an individual. The package would be used in association with a consumer prompting device that both reads information from the package and writes information onto the package with regard to use of the medication. The information with regard to the use of the package is stored on the interactive memory unit, that is information with regard to a method of determining the next take time. Information with regard to the method of determining the next take time is transferred to the consumer prompting device wherein the next take time is calculated and the next take time is stored on the consumer prompting device and the method of determining next take time is deleted from the consumer prompting device. In addition, if the consumer takes a medication the take time is written from the consumer prompting device to the interactive memory unit Thus, all information with regard to the medication is stored with the package. The advantage of the system herein is that the consumer prompting device does not store each method of determining the next take time for each medication, rather it obtains the method from the package, calculates the next take time and then deletes the method. Accordingly, the memory requirements for the consumer prompting device can be greatly reduced. In addition information with regard to use of a medication could also be stored with the consumer prompting device.

Accordingly, it would be advantageous to provide a package that includes a memory unit that stores information with regard to the medication and in addition stores information with regard to the use thereof. Thus the package could electronically store information with regard to the medication and its incompatibilities, the particular regime for a particular individual, and information with regard to corrective measures when the medication is not taken in accordance with the preferred instructions. When such a package is used with a consumer prompting device, the device can prompt the individual with regard to the regime and the consumer prompting device can write back onto the memory unit in the package information with regard to use of the medication. The consumer prompting device can be arranged such that the prompt for taking the medication can only be deactivated by the particular package. Further, the consumer prompting device may prompt for refills, provide a second log of the use of a particular medication, and provide a positive identification of the individual with the package. The consumer prompting device may include a display that advises regarding corrective measures where the prescribed regime was deviated from.

Such a package in association with a consumer prompting device would provide a number of advantages. Information with regard to the use of the medication would be attached to the package of medication. This would help the health care professional to diagnose the individual when considering symptoms and further medications. Further, such information would be useful for clinical studies with regard to the use of medication. Further, the package in association with the consumer prompting device provides a system of verification to help reduce the chance of an individual taking a medication at the wrong time or in association with incompatible medications.

SUMMARY OF THE INVENTION

An interactive reminder device includes a read/write module, an integrated circuit, a power supply, memory, a clock and a prompt. The read/write module is adapted to read Information stored on an identifiable integrated circuit chip and to write information onto the identifiable integrated circuit chip attached to a package. The integrated circuit is operably connected to the read/write module. The power supply is operably connected to the integrated circuit. The memory is operably connected to the integrated circuit. The dock operably connected to the integrated circuit and the prompt is operably connected to the integrated circuit. The interactive reminder device is for use with a package having an integrated circuit chip attached thereto.

In another aspect of the present invention there is provided a system for prompting for the use of medication. The prompting system includes the steps of reading information stored on an integrated circuit chip regarding a method of calculating a next take time; calculating the next take time; storing a next take time In a prompting device; and prompting at the next take time.

In a further aspect of the invention the prompting system is adapted for use in a health care facility. The health care facility steps include calculating the next take time for an identifiable patient for an identifiable medication; storing a next take time, the identified medication and the identified patient in a prompting device; prompting at the next take time; confirming that the medication integrated circuit chip is the medication integrated circuit chip associated with the identified medication; and confirming that the patient integrated circuit chip is the patient integrated circuit chip associated with the identified patient and thereafter administering the identified medication to the identified patient.

As still further aspect of the present invention Is a package having an integrated circuit chip integrally attached thereto whereby removing the chip destroys the package.

Further features of the invention will be described or will become apparent in the course of the following detailed description.

BRIEF DESCRIPTION OF THE DRAWINGS

The invention will now be described by way of example only, with reference to the accompanying drawings, in which:

FIG. 7 is a bottom view of the consumer prompting device of FIG. 4;

FIG. 10 a top view showing the pill container of FIG. 8 in contact with the consumer prompting device of FIG. 4;

FIG. 21 is a flow chart showing the logic steps of the consumer prompting device: and FIG. 22 is a flow chart showing the use of the present invention in a health care facility,

DETAILED DESCRIPTION OF THE INVENTION

Figure 1:
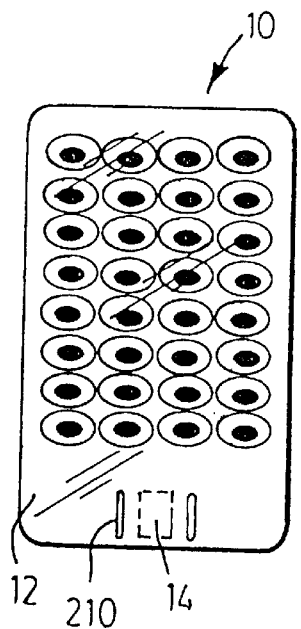
FIG. 1 is front view of a blister pack for pills having an integrated circuit chip embedded therein in accordance with the present invention.
Figure 2:
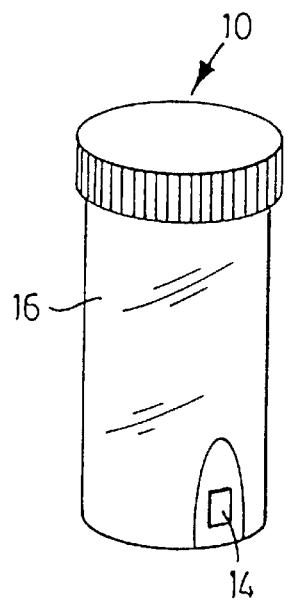
FIG. 2 is a perspective view of a pill container having an integrated circuit chip embedded therein in accordance with the present invention.
Figure 3:
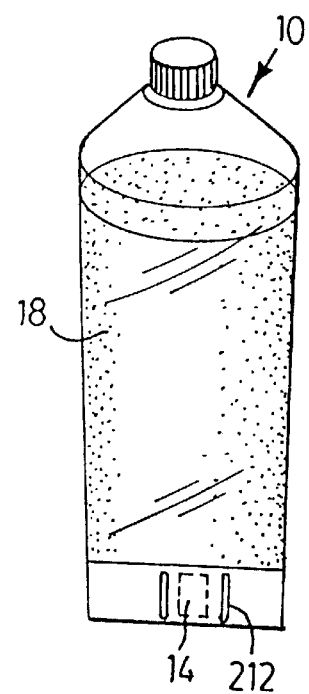
FIG. 3 is a front view of a tube of medication having an integrated circuit chip embedded therein in accordance with the present invention.
Figure 4:
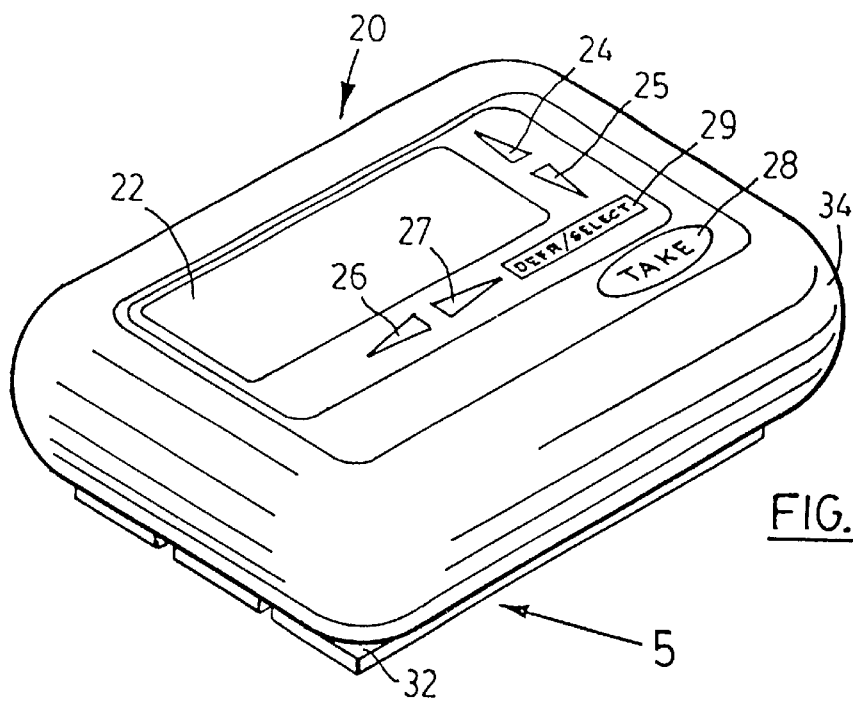
FIG. 4 is a top perspective view of a consumer prompting device in accordance with the present invention.
Figure 5:
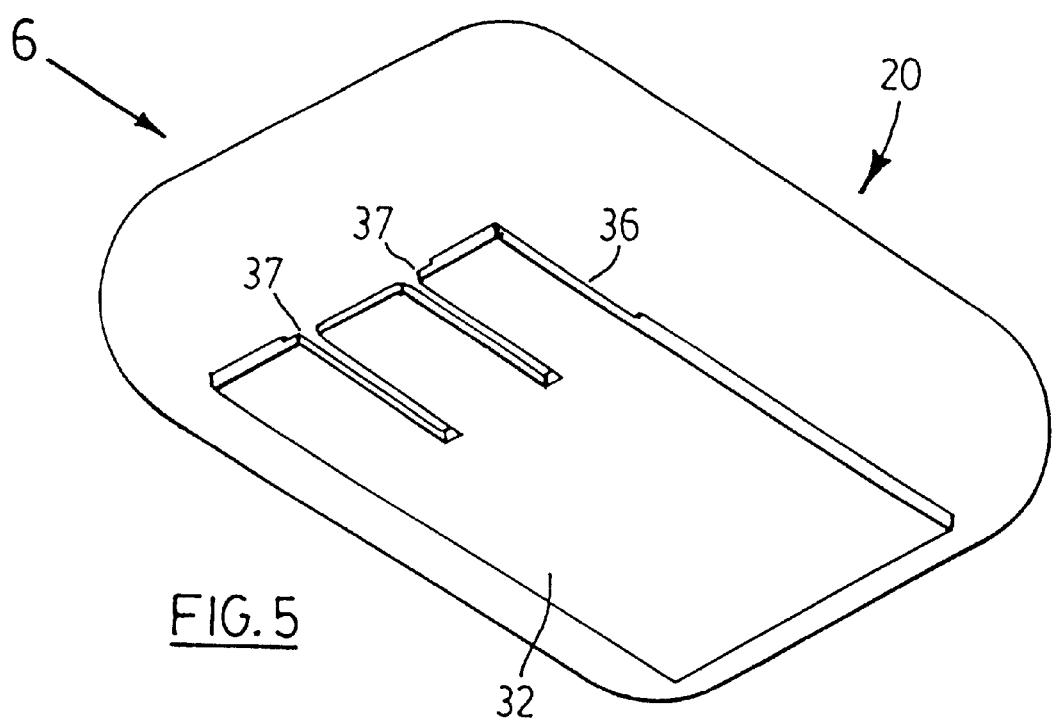
FIG. 5 is a bottom perspective view of the consumer prompting device of FIG. 4 as viewed from arrow 5.
Figure 6:
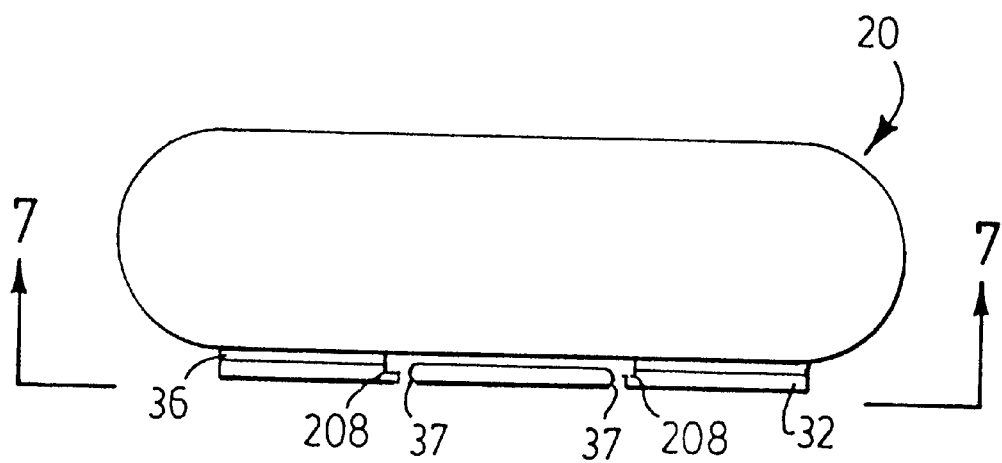
FIG. 6 Is an end view of the consumer prompting device of FIG. 5 as viewed from arrow 6.

Referring to FIGS. 1 through 3, a package with an integrated circuit chip attached thereto is shown generally at 10. Three different examples of packages are shown in FIGS. 1 through 3. Specifically, FIG. 1 shows a blister pack 12 with an integrated circuit chip 14 attached thereto, FIG. 2 shows a bottle 16 with an integrated circuit chip 14 attached thereto and FIG. 3 shows a tube 18 with an integrated circuit chip 14 attached thereto. Preferably, integrated circuit chip 14 is embedded in the package 10 such that removing the integrated circuit chip 14 results in damaging the package.

The integrated circuit chip 14 is used to store information about the product in the package and about the use of the package. This is of particular importance in regard to the medications. Specifically, information with regard to a method of calculating the next take time is stored on the integrated circuit chip 14. As well information regarding the medication such as best practices regarding administering the medication, incompatible medications, amount of medication in the package, and corrective action if the medication is not taken in accordance with the best practices may be stored on the integrated circuit chip 14. In addition the integrated circuit chip can include information specific to the patient such as patient identification and the specific regime for the patient. The integrated circuit chip can also store information with regard to the dates and times the medication was used.

Figure 18:
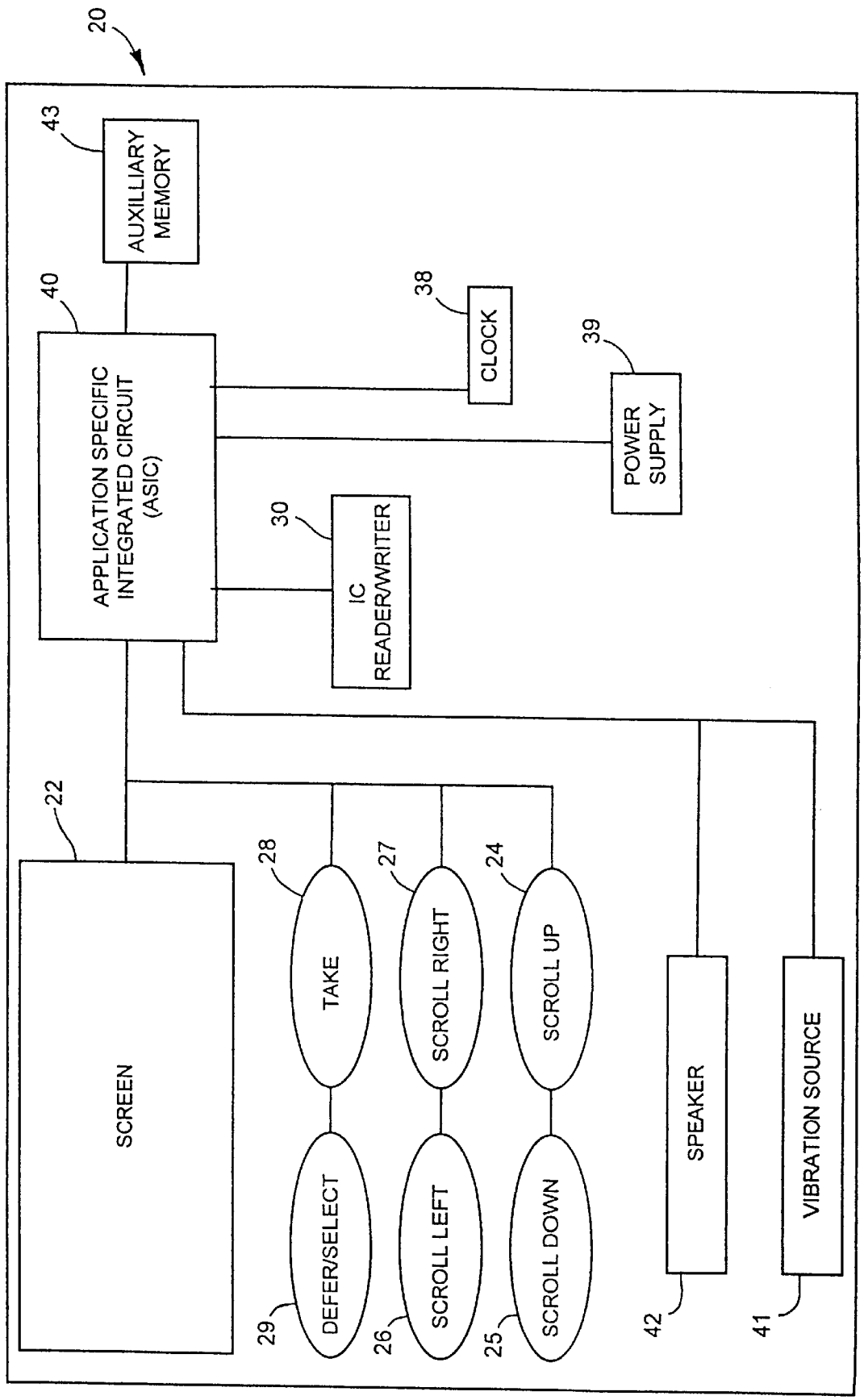
FIG. 18 is a block diagram of the elements inside a consumer prompting device.

Referring to FIGS. 4 to 7, consumer prompting device is shown generally at 20. Consumer prompting device 20 includes a display 22, a scroll up arrow shaped button 24, a scroll down arrow shaped button 25, a scroll left shaped button 26 and a scroll right shaped arrow 27. The scroll buttons 24, 25 allow the user to scroll the information in the display screen up or down respectively. Scroll buttons 26 and 27 allow the user to scroll the information in the display screen left and right respectively. In addition there is a TAKE button 28 and a DEFER/SELECT button 29. Consumer prompting device 20 has a read/write module 30, shown in FIG. 18. Read/write module 30 is a contact type read/write module wherein contact is required. Consumer prompting device 20 can be any size or shape desired. Preferably consumer prompting device is the size of a pager.

Figure 13:
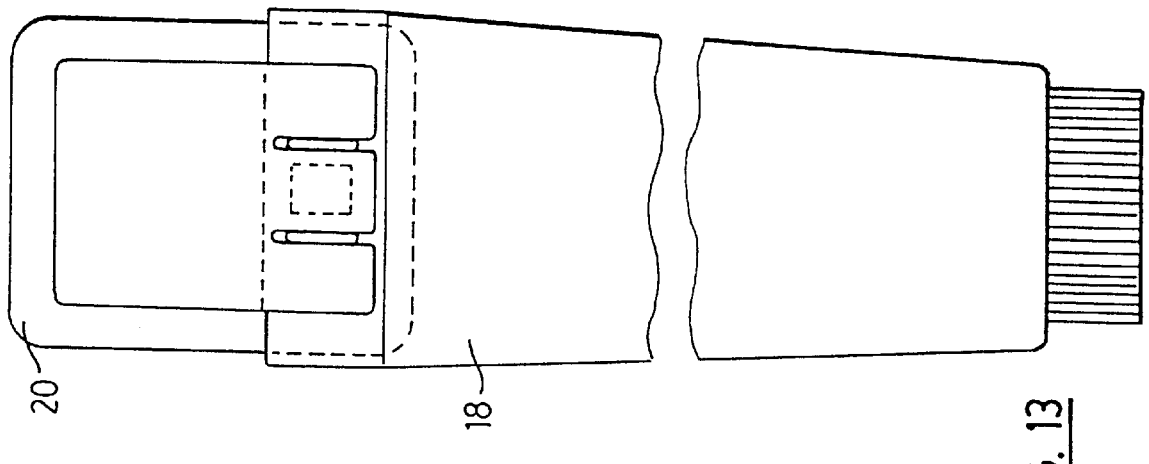
FIG. 13 is a bottom view of a tube of FIG. 3 moving into contact with the consumer prompting device of FIG. 4.
Figure 12:
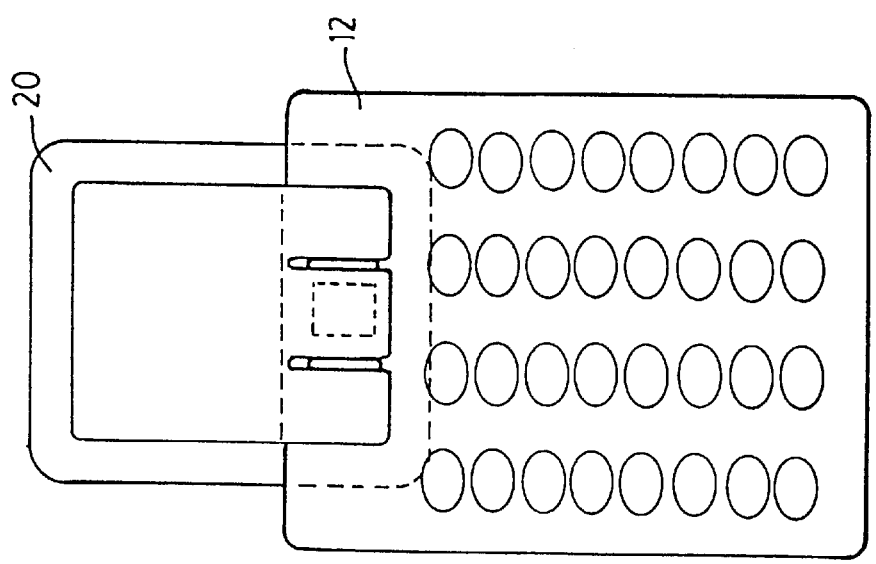
FIG. 12 is a bottom view of a blister pack of FIG. 1 moving into contact with the consumer prompting device of FIG. 4.

A read/write station 32 is attached to case or housing 34. Read/write station 32 includes a longitudinal slot 36 and a pair of transverse slots 37. The longitudinal slot 36 facilitates bringing the integrated circuit chip 14, in blister pack type packages 12 or tube 18 as shown In FIGS. 12 and 13 respectively, into contact with the read/write module 30 housed in the consumer prompting device 20. Since longitudinal slot 36 is open at each end there is no restriction in the width of blister type packages 12 or tubes 18 that can be used. Transverse slots 37 are used to position the integrated circuit chip 14 in the read/write station 32 such that integrate circuit chip 14 is in contact with read/write module 30 in the consumer prompting device 20.

Figure 8:
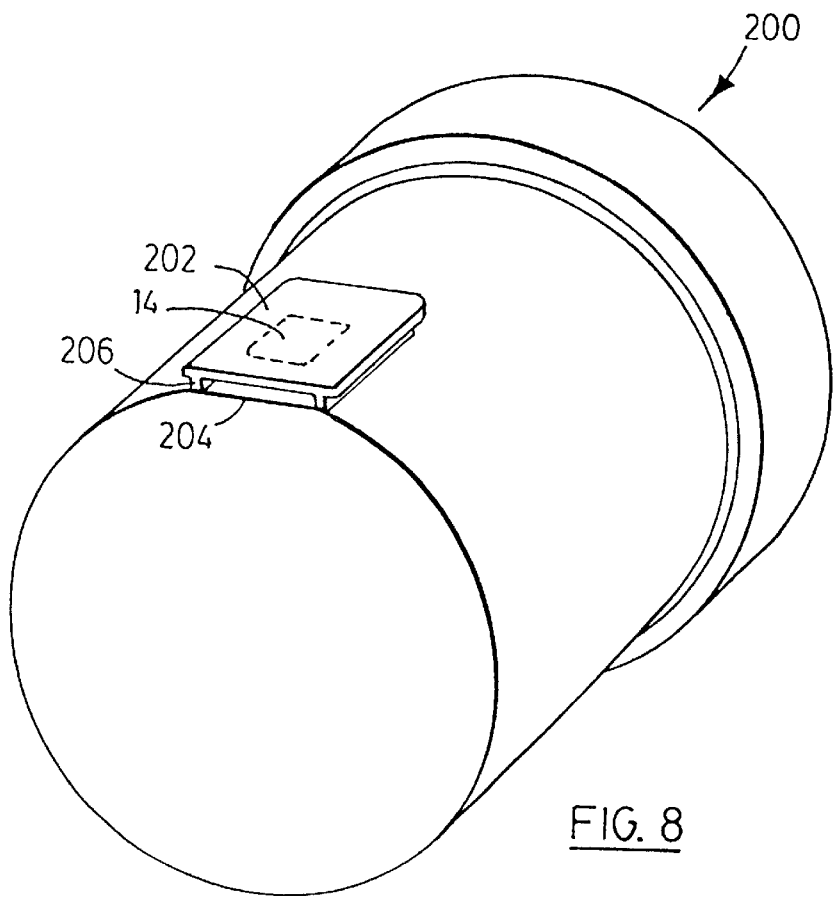
FIG. 8 an enlarged perspective view of a pill container.
Figure 9:
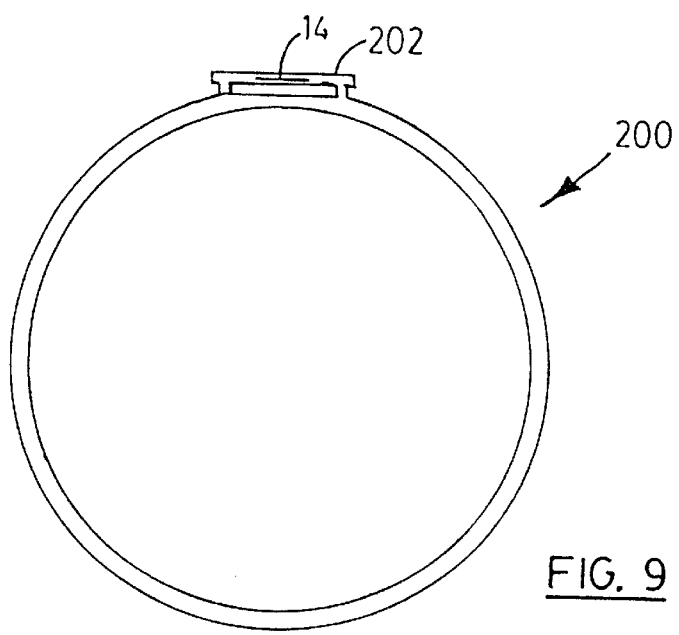
FIG. 9 is an end view of the pill container of FIG. 8.
Figure 11:
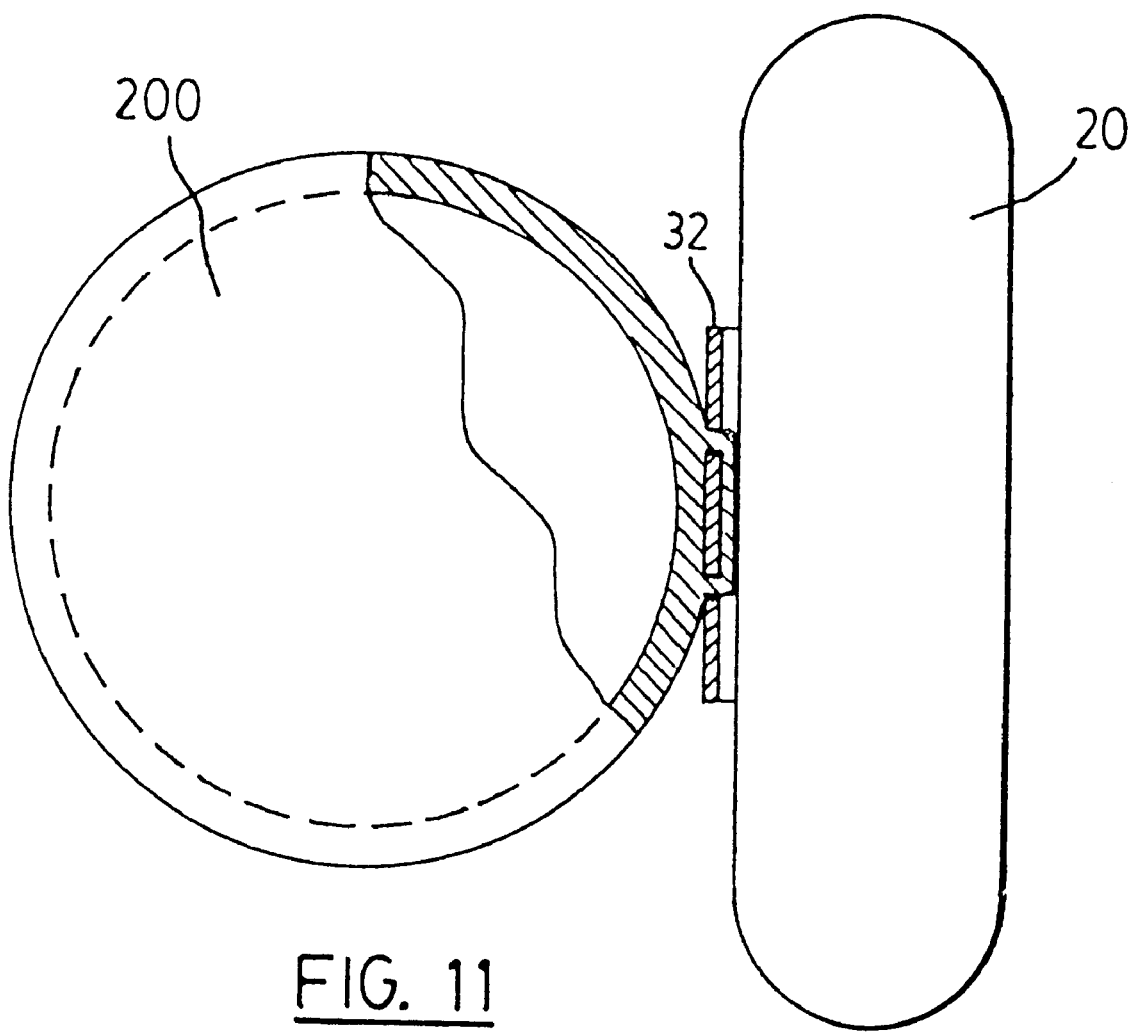
FIG. 11 is a cross sectional view of the pill container in contact with the consumer prompting device taken along line 11 of FIG. 10.

Referring to FIGS. 8 to 10 a bottle 200 includes an integrated circuit chip 14 that is attached to a plate 202 that is spaced from bottle wall 204. Legs 206 are attached to bottle wall 204 and plate 202 and hold plate in position. Since the plate 202 is spaced from the wall 204 bottle chip 14 can come into contact with reader/write module 30 as shown in FIGS. 10 and 11. Legs 206 slide into transverse slots 37. Transverse slots 37 are provided with ledges 208 to further aid in the positioning of the bottle 200 in reader/writer station 32.

The integrated circuit chip 14 in blister type package 12 is positioned in the read/write station 32 as shown in FIG. 12 so that chip 14 is in contact with reader/writer module. Blister type package 12 includes a pair of spaced apart ridges 210 are positioned on either side of Integrated circuit chip 14 and are positioned to be in registration with transverse slots 37 when the blister type package 12 is positioned in the reader/wrter station 32. Similarly, the integrated circuit chip 14 in tube 18 is positioned in read/write station 32 as shown in FIG. 13 so that chip 14 is brought into contact with reader/writer module. Blister type package 12 Includes a pair of spaced apart ridges 212 are positioned on either side of integrate circuit chip 14 and are positioned to be in registration with transverse slots 37 when the tube 18 is positioned in the reader/writer station 32.

Figure 17:
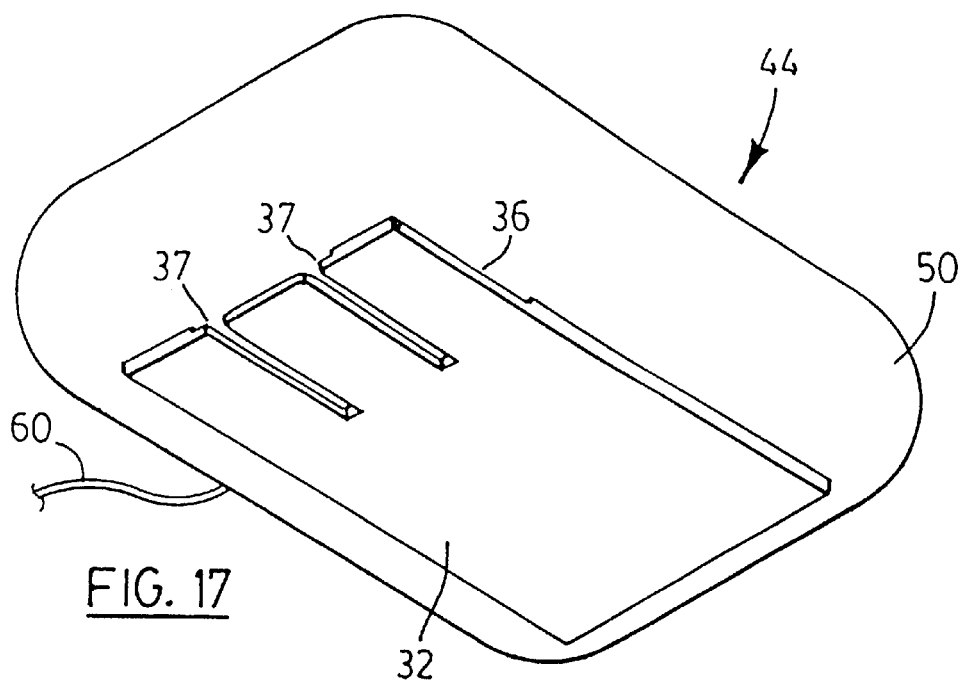
FIG. 17 is a bottom perspective view of a device used by a health care professional shown in FIG. 15.

Referring to FIG. 17, consumer prompting device 20 includes a clock 38, a reader/writer module 30, a screen 22, a power supply 39, an integrated circuit 40, scroll buttons 24, 25, 26, and 27, TAKE button 28, DEFER/SELECT button 29, vibration source 41 and speaker 42. In addition there may be auxiliary memory 43. Preferably the screen 22 is a liquid crystal screen. The integrated circuit 40 is an application specific integrated circuit. Preferably the power supply 39 is an AA battery. Alternatively or in addition, the consumer prompting device could include a light indicator.

A menu screen with the aid of the scroll buttons 24, 25, 26 and 27 will make available all of the information stored in the consumer prompting device 20. Specifically information such as viewing the medication list and the next take times, the date and time set, time zone adjustments, volume control for the audio prompt, selecting prompt method, and delete and stop medication. Preferably the user can select the prompt from a menu including vibration, various audio prompts and a visual indicator on the screen, When the integrated circuit 14 is read by the read/write module additional information is available through the menus on the screen, namely best practices, contra indicators and hazards.

In addition the frequency and dosage for the medication, the prescribing physician and any other information stored on the integrated circuit chip 14 are available.

Device 20 would record the number of times that the date and time set was adjusted. This would allow the health care professional to determine if the record of take times is accurate and to ensure that the user cannot circumvent the monitoring aspect of the present system by changing the date and time set to falsely record the date and time a medication was taken.

Figure 14:
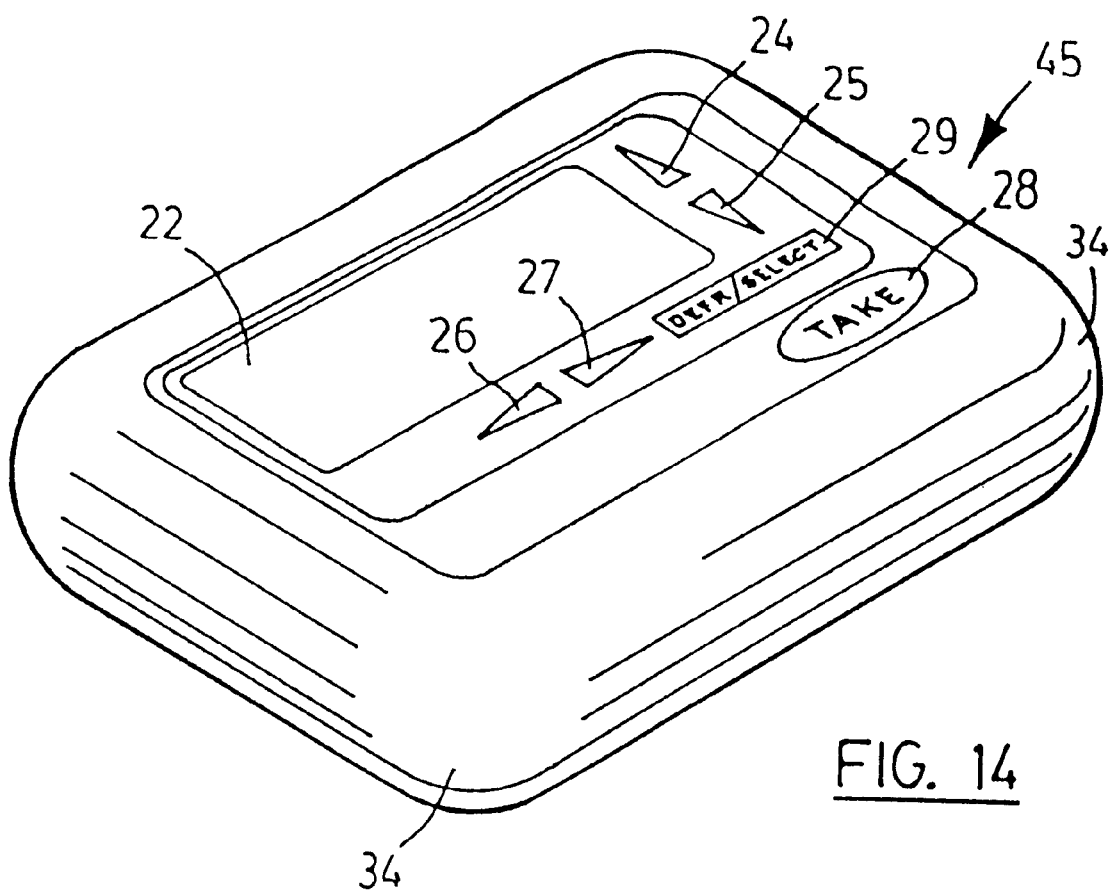
FIG. 14 is a perspective view of an alternate embodiment of the consumer prompting device using a contactless system.

Referring to FIG. 14 alternatively, a contactless read/write module is used in the consumer prompting device 45. The main difference between consumer prompting device 45 and device 20 is that device 45 includes a contactless read/write module. Accordingly consumer prompting device 45 does not require a read/write station per se, since the integrated circuit chip 14 need not actually contact the contactless read/write module. The contactless read/write module is positioned proximate to the surface of the device 45. To facilitate use of a contactless read/write module an antenna is provided in the package attached to the integrated circuit chip 14. In use the integrated circuit chip 14 is brought Into proximity with the contactless read/write module and information is transferred between the consumer prompting device and the integrated circuit chip. Thus the consumer can "swipe" the package by device 45 to exchange information. Preferably consumer prompting device 45 will indicate when information has been transferred The Indicator could be a visual indicator, a sound or the like.

It will be appreciated by those skilled in the art that the consumer prompting device 20, 45 could be incorporated into a palm pilots™ or an electronic personal organiser, In particular the read/wrter module and a read/write station where required could be incorporated into such a unit. Thus the consumer would not need to carry a separate device.

Referring to FIG. 2, a bottle 16 is shown with an integrated circuit chip 14 embedded therein. This type of bottle 16 is for use with a contactless consumer prompting device 45. With regard to blister type package 12 and tube 18 ridges 210 and 212 respectively need not be included.

Figure 15:
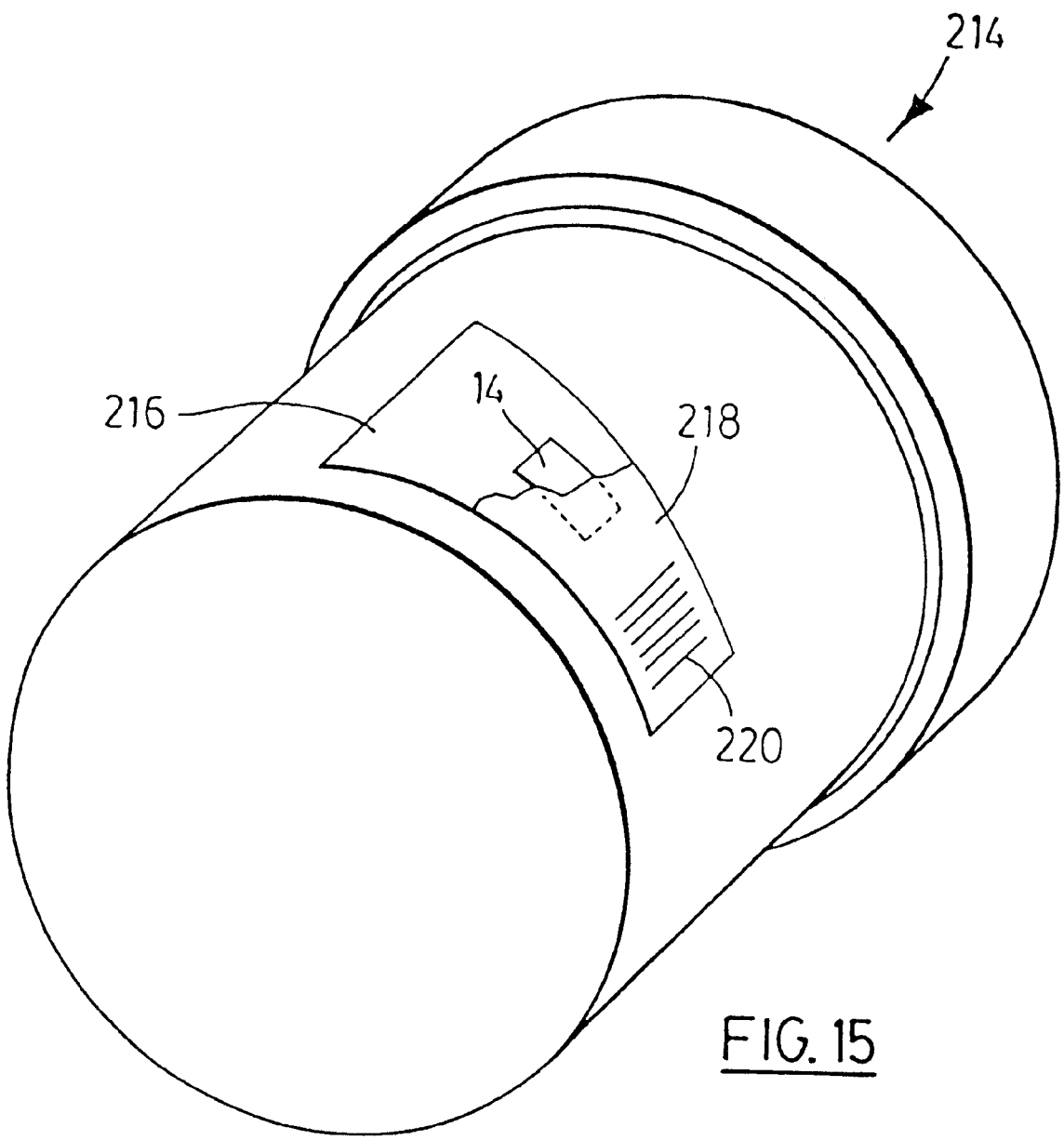
FIG. 15 is a perspective view of a pill container having an integrated circuit chip attached thereto with a label with a portion of the label shown broken away.

Referring to FIG. 15, a bottle 214 is shown with the integrated circuit chip 14 attached thereto with a label. The label includes an adhesive layer 218, the integrated circuit chip 14 and a top layer 218. Top layer may include any information desired by the user including a bar code 220.

Figure 16:
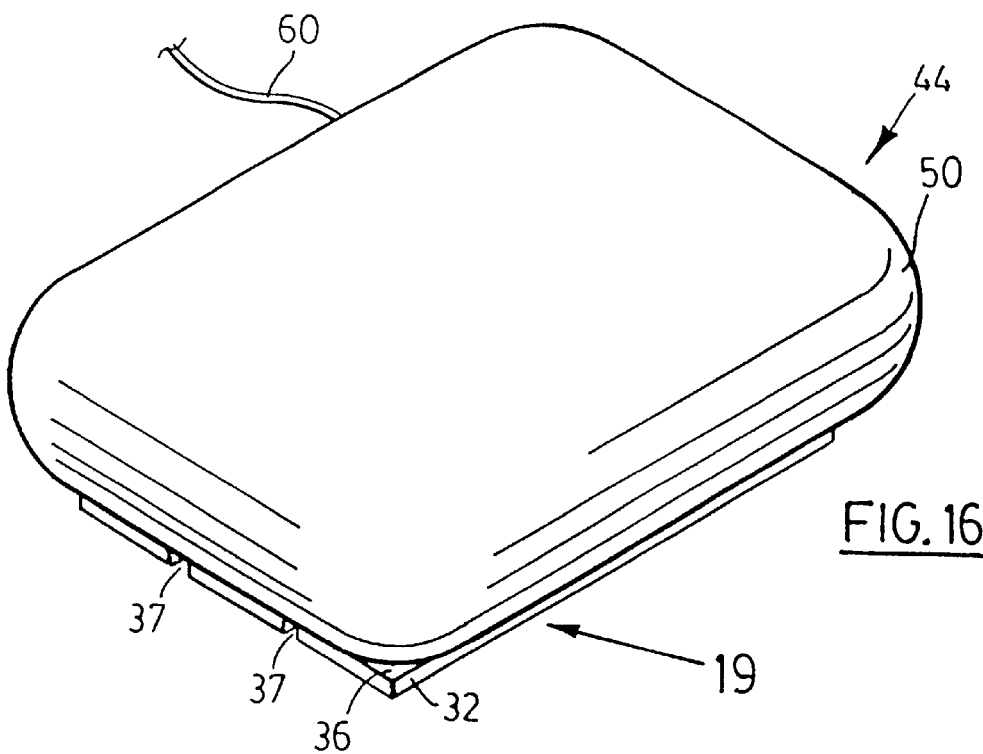
FIG. 16 is a top perspective view of a device used by a health care professional in accordance with the present invention.

Referring to FIGS. 16 and 17 a reader/writer 44 is for use by a health care professional such as a retail pharmacist, a hospital pharmacist, a doctor, a doctor's assistant and the like. Reader/writer 44 is somewhat similar to the consumer prompting device 20 discussed above. Reader/writer 44 has a chip read/write module. Similar to consumer prompting device, read/write module is a contact type read/write module wherein contact is required. Accordingly, a read/write station 32 as described above is provided in the case 50 of reader/writer 44 to facilitate bringing the integrated circuit chip 14 in blister pack type packages 12 or tube 18 in contact with the read/write module. Case 50 also includes a read/write station 52 for a bottle 16 type package. The reader/writer 44 is connected through cable 60 to the health care professional's computer (not shown) for inputting information into the integrated circuit chip 14 in the package. Information specific to the patient or consumer is written onto the integrated circuit chip 14. In addition information such as contra indicators, warnings, cautions or procedures to take if a patient fails to take the medication at the prescribed time may be written onto the integrated circuit chip by the health care professional or by the pharmaceutical company if it is an integrated circuit chip that is always associated with a specific medication. It will be appreciated by those skilled in the art that alternatively if desired a single purpose reader/writer unit could be developed for inputting the information onto the integrated circuit chip rather than connecting the reader/writer 44 to the health care professional's computer.

A package having an integrated circuit chip 14 attached thereto could be used in monitoring the flow of packages in a number of different applications. The application described hereafter is for use with regard to monitoring and prompting for the correct use of medications. In order to facilitate the correct use of the medications a number of systems need to be implemented. Specifically there is a system for obtaining the information specific to a patient or consumer and writing it on an integrated circuit chip attached to the medication; a system for ensuring that the patient takes the right medication at the prescribed time; a system used by the consumer prompting device to prompt the patient or consumer, and a system that modifies the above systems for use in a health care facility.

Figure 19:
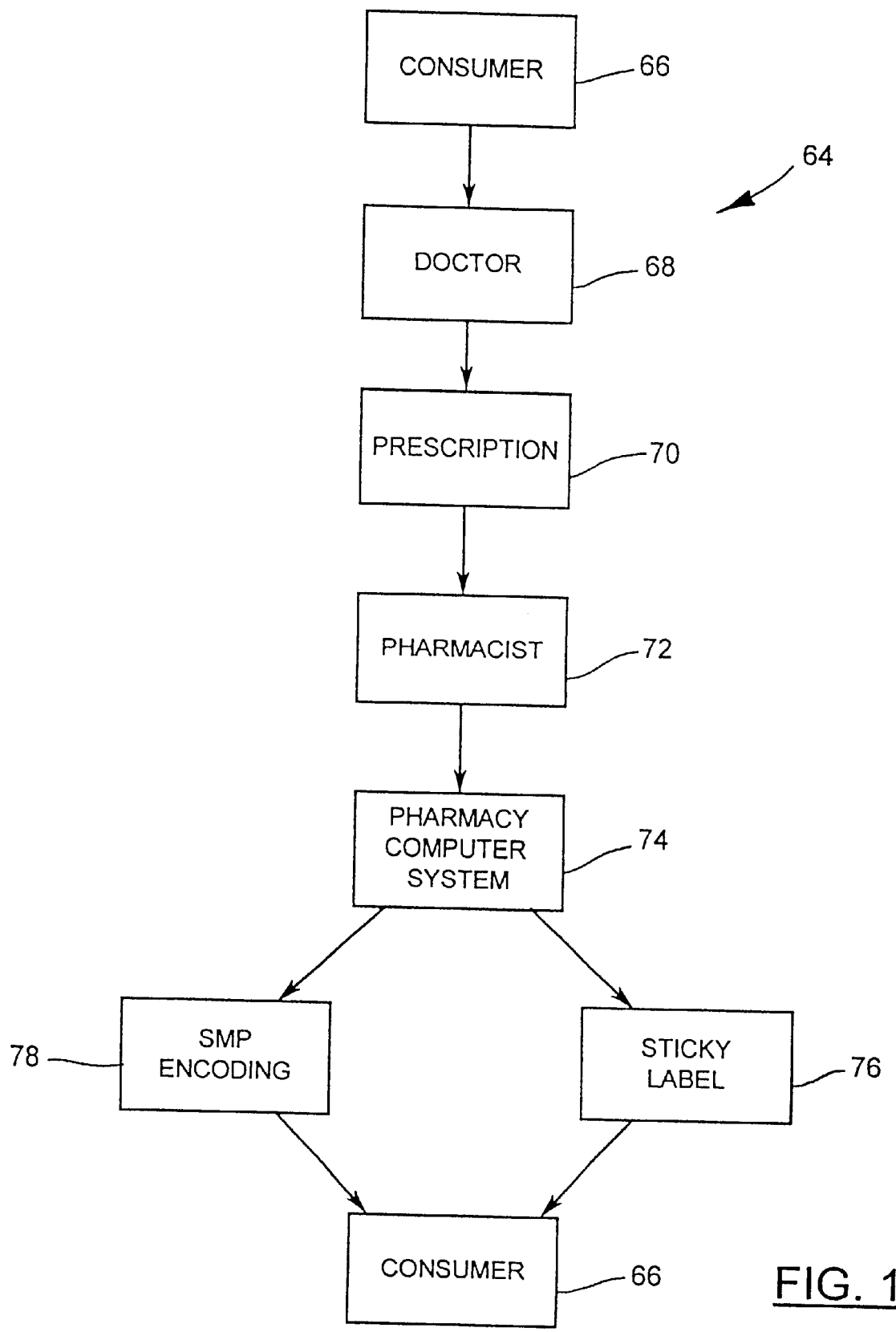
FIG. 19 is a flow chart showing the steps used to program an integrated circuit chip attached to a package.

Referring to FIG. 19 the steps for obtaining the information specific to a patient or consumer and writing it on an integrated circuit chip attached to the medication is shown generally at 64. The patient or consumer 66 is attended to by a doctor 68. The doctor provides a prescription 70. The prescription may be in the form of the traditional written script or electronic information that is provided on a smart-card or the like. The patient 66 attends at a pharmacy and the pharmacist 72 inputs information with regard to the prescription 70 in the pharmacy computer system 74. The pharmacy computer system 74 generates a sticky label 76 and encodes 78 information onto the integrated circuit chip 14. Information such as prescribed manner of taking medication including time and dosage is encoded or written onto the integrated circuit chip, as well the method of calculating the next take time is encoded or written onto the integrated circuit chip. In addition, information with regard to best practices, contra indicators and hazards is written onto integrated circuit chip 14. The medication with the sticky label 76 and integrated circuit chip 14 attached thereto is given to the consumer or patient 66.

Information such as the contra indicators and hazards may be written onto the integrated circuit chip 14 by the pharmaceutical company prior to shipping. This provides the pharmaceutical company with the opportunity of updating the information with regard to best practices, contra indicators and hazards as soon as the information is available. The method of calculating the next take time could include a wide range of variables. Preferably the next take time includes a take window wherein the next take time is the preferred take time but there is a time range where taking the medication is acceptable. This would be useful for a user who wanted to take a medication prior to starting an activity, the user could insert the medication package 10 into the consumer prompting device 20 and determine if the time is within the take window. Preferably the next take time also includes defer parameters. For example in the case of certain conditions wherein failure to take the medication at the prescribed time is life threatening if user defers taking the medication the device will prompt again in a very short period of times. Alternatively where failure to take the medication at the prescribed time is not life threatening the prompt may be deferred for a longer period of time. In addition preferably information with regard to the number of medications will be included in the information stored on the Integrated circuit chip 14 and when the date and time of take a medication the amount left will be updated. Thus when a predetermined amount of medication is left Information with regard to a obtaining a refill will be transferred to the prompter which will prompt the consumer to buy a refill.

Figure 20:
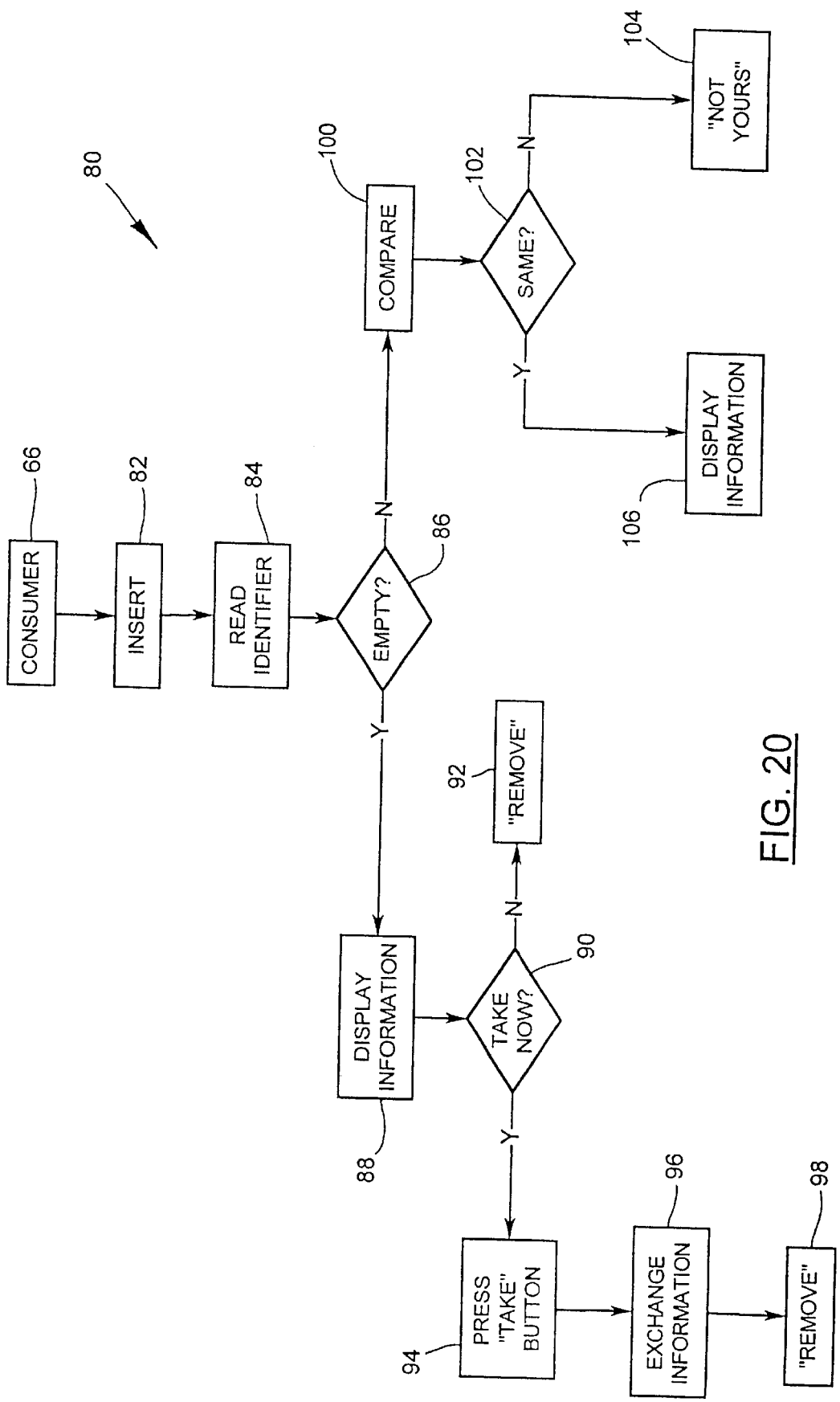
FIG. 20 is a flow chart showing the steps used by the individual.

The steps that the patient takes in association with a package having an integrated circuit chip 14 and the consumer prompting device 20 for ensuring the right medication at the prescribed time is shown generally at 80 in FIG. 20. The consumer or patient 66 inserts 82 the package or medication with the integrated circuit chip 14 into the consumer prompting device 20. The consumer prompting device reads the unique identifier 84 on the integrated circuit chip 14 attached to the medication. Device 20 determines if the field is empty 86. If the field is empty it Is a new package and the information in the integrated circuit chip 14 Is then read and displayed 88, including such information as best practices with regard to taking the medication, contra indicators and hazards. In addition, a unique identifier is written onto the integrated circuit chip 14 of the package 10. Device 20 reads the method of calculating the next take time and determines if the medication should be taken now 90. If no, the package is removed 92 from the consumer prompting device. If yes and the patient intends to take the medication now, the TAKE button is pressed 94, information regarding the taking of the medication is exchanged 96 between the consumer prompting device 20 and the integrated circuit chip 14. Information regarding the method of determining the next take time is transferred temporarily from the integrated circuit chip 14 to device 20 wherein the next take time is calculated and stored. Thereafter the method of calculating the next take time is deleted from device 20. Information regard the date and time of the patient taking the medication is transferred from the device 20 to the integrated circuit chip 14. Thereafter the consumer is prompted 98 to remove the package from device 20. On the other hand if the unique identifier field is not empty, device 20 compares 100 the unique identifier with identifiers stored on the consumer prompting device 20. If device 20 does not have the same identifier 102, then the package with the integrated circuit chip 14 is not for use in association with that particular consumer prompting device 20 and it will display 104 "NOT YOURS" and prompt for the package to be removed from device 20. Alternatively, if the identifiers are the same 102 it is a package that is to be used in association with that particular consumer prompting device 20 and information stored on the integrated circuit chip 14 is displayed 106. Preferably the information displayed includes the drug name, the next take time and if the time is currently within the take window, best practices, contra indicators, hazards, prescribing physician and the like.

Referring to FIG. 21 the logic steps of the consumer prompting device 20 to prompt the patient or consumer is shown generally at 108. For the consumer prompting device to be in the active mode the power is on 110. Device 20 loops through the "next take" fields 112. Device 20 determines if the "next take" fields are null 114. If the "next take" fields are not null, that is there is information in the "next take" fields, device 20 determines if the date and time in the "next take" field is the same as the current date and time 116. If no, device 20 goes back 118 to looping through the "next take" fields 112. On the other hand, if the date and time in the "next take" field is the same as the current date and time, then device 20 prompts to take the medication and displays contra indications 120. The prompt may be an audio prompt, a vibration or a visual prompt or a combination thereof. The patient then decides 122 either to take the pill immediately or to defer taking the pill. If the patient chooses to take the medication, then the patient presses TAKE 124. Device 20 prompts 126 the consumer to insert 128 Integrated circuit chip 14 associated with a specific medication. Device 20 compares the identifier In the integrated circuit chip 14 with the identifier associated with the "next take" field 130. If the identifiers are correct 132, information regarding the date and time is exchanged and stored 134. That is, information regarding the method of determining the next take time is transferred temporarily from the integrated circuit chip 14 to device 20 wherein the next take time is calculated and stored. Thereafter the method of calculating the next take time is deleted from device 20. Information regard the date and time of the patient taking the medication is transferred from the device 20 to the integrated circuit chip 14. Thereafter, device 20 prompts the patient to remove the package 136 and then goes back to looping through the "next take fields" 112. However, if the identifiers are incorrect, the message INCORRECT is displayed 138 and the device goes back to prompt 126 the consumer to insert an integrated circuit chip associated with the medication. If the patient cannot take the medication at the time of being prompted, the consumer may press the DEFER button 140. Thereafter the defer processing steps are performed 142 which include updating the date and time for the "next take" field. Thereafter the device goes back 144 to the step of looping through the "next take" fields 112. In the event that the information in the "next take" fields is null, that is no medications are scheduled to be taken, device 20 goes to lower power mode 148. After a predetermined time the system goes back to the power on step 110 and starts the process again.

It will be appreciated by those skilled in the art that the information regarding the date and time patient took the medication could be stored on the integrated circuit chip 14 as discussed above. However, that information could also be stored on the consumer prompting device as well or on another integrated circuit chip such as smartcard health card that contains all patient's health information.

The devices described above can be readily adapted for use in a health care facility such as a hospital. Referring to FIG. 22, the system for a health care facility is shown at 148. The main components of the hospital system include a hospital medication container 158, independent work station 154 and the nurse prompter 162.

Hospital medication container 158 includes an integrated circuit chip 14. In a typical hospital, medications are dispensed from central and distributed hospital pharmacies to floor nursing stations or floor pharmacy stations, and then transferred to trays of open containers marked with patient names, floor and room numbers. The hospital medication container 158 includes an integrated circuit chip 14 that is preferably fabricated into a protruding, reinforced 'lip' of the container, which would facilitate the attachment of the container to a hand held reader/wrter unit in the nurse prompter 162 and a reader/writer 156 attached to the workstation 154.

Workstation 154 would run nurse prompter host application software, with attached Reader/Writer unit, and infrared link port: this independent workstation (Win 95/98/NT, MacOS, or Unix based) would be running the nurse prompter host application software that performs functions supporting the operation of the Nurse prompter (e.g. loading Information into Nurse prompter, synchronizing information on Nurse prompter and Nurse prompter-Host, displaying information stored on any Nurse prompter, printing reports, backing up Nurse prompter date, etc.). The attached Reader/Writer 156 is where hospital medication container 158 is attached when interacting with the Nurse prompter-Host application. The infra-red link port between a keyboard cradle 152 is used to communicate and exchange data with nurse prompters 162. Thus the keyboard cradle 152 can be used to input information into the nurse prompter 162.

Preferably the nurse prompter 162 uses off-the-shelf hardware as the base unit for the nurse prompter (e.g. existing or future versions of personal hand-held electronic organizers with sophisticated operating systems, such as the Palm Pilot™, running a Java JVM (Java Virtual Machine) under the Palm OS, or a PSION Series 5MX running a JVM under EPOCH. A reader/writer is added to this base hardware. The reader/writer can be a contact type or a contactless type. The software developed to drive the nurse prompter 162 functionality would use the development tools of the OS of a particular electronic organizer. Interaction with the software would be via the stylus activated touch screens and/or attachable keyboards of the organizers. The nurse prompter 162 could be associated with any group of rooms/beds, and information could be passed between nurse prompters 162.

Referring to FIG. 22, the hospital system has a number of steps that are common to the individual system described above. The patient would be seen by a doctor 68 and more specifically a hospital doctor who would write a prescription 70. The prescription information would be given to the floor nursing station staff or the staff responsible for administering the medication to the patient 150. The prescription information would also be given to the hospital pharmacy computer system. The information would be given to the floor pharmacy station 164 or the unit responsible for dispensing the medication. The pharmacy station 154 would be connected to a read/writer 156 similar to the reader/writer 44 above. It would encode information onto the integrated circuit chip 14 attached to the hospital smart medication container 158. A plurality of hospital medication container 158 can be put in a hospital medication cart 160 for easy transportation to the patients, The nurse prompter 162 is somewhat similar to the consumer prompting device 20 but it would display additional information such as a patient identification number 164 and a room number 166. The information could be encoded directly into its integrated circuit chip from the hospital reader/writer 156 or from the information on the hospital smart medication container 158. In use, when the nurse prompter 162 indicates that a medication is due the nurse would need to verify that it is the correct medication by reading the information on the integrated circuit chip 14 attached to the hospital medication container 158 and to verify that it is the correct patient by reading the information on the integrated circuit chip 170 attached to the patient's identification bracelet 168. During this verification process information related to the distribution of the medication would be exchanged between the nurse prompter and the patient integrated circuit chip 170 and between the hospital smart medication container 14. This system will help to reduce the likelihood of administering a medication to a patient more than once. Further, the doctor or other health care professional will be able to read the information on the patient Identification bracelet 168 to monitor the amount and time of medication.

The system of the present invention is very user friendly and it is designed so that a user can easily use the device without a lengthy training period. Following sets out the steps a typical example of the use of the consumer prompting device 20 of the present invention:

the user installs a battery and sets the date and time and time zone on the user prompting device 20;

user goes to doctor and is given prescription for one or more medications;

user goes to pharmacy and submits prescription (time is 12:00 noon);

depending on the packaging style used by the pharmaceutical firm for the prescribed medication, the pharmacist would follow the following steps:

a. PHARMACIST COUNTS OUT PILLS FROM A BULK CONTAINER RECEIVED FROM PHARMACEUTICAL FIRM pharmacist enters the prescription into his pharmacy computer system (a database including a record, by user name, of all prescriptions issued to that user);

usually a prescription from a physician includes: name of medication and dosage/strength, number of pills (or some other measure of quantity) and frequency, number of repeats allowed, name of user, prescribing doctor, date issued;

pharmacist places empty bottle 16, 200 into pharmacy reader/writer unit 44;

upon issuing a command, the modified pharmacy computer system software would both print a standard exterior stick-on label and write the prescription Information onto the integrated circuit chip 14 attached to bottle 16, 200;

simultaneously, the pharmacy computer system software would write additional information pertaining to the medication onto the integrated circuit chip 14—this information would originate from the pharmaceutical manufacturer and could be integrated in to the pharmacist's computer system software in a variety of ways (including via updates through the Internet or via information updates supplied on Smart Cards) . . . this additional information pertaining to the medication would include: warnings, contra-indications, corrective measures in the event of an error in self medication, encoded ranges used by the consumer prompting device 20 to calculate the take windows—the time in which it will issue directions to the user to take a medication, encoded safe prescribing ranges used by the consumer prompting device 20 to cross check prescribing information issued by the doctor;

pharmacist places the sticky-label on the exterior of bottle 16, 200 and fills the bottle with the correct quantity of pills;

pharmacist gives bottle 16, 200 to user;

b. PHARMACEUTICAL FIRM PRE-PACKAGES THE MEDICATION IN A BLISTER PACK 12 OR TUBE 18 pharmacist enters the prescription into his pharmacy computer system;

usually a prescription from a physician includes: name of medication and dosage/strength, number of pills (or some other measure of quantity) and frequency, number of repeats allowed, name of user, prescribing doctor, date issued;

the integrated circuit chip 14 on blister packs 12 or tube 18 of medication would already contain warnings, contra-indications, corrective measures in the event of an error in self medication, encoded ranges used by the consumer prompting device 20 to calculate the take window, encoded safe prescribing ranges used by the consumer prompting device 20 to cross check prescribing information issued by the doctor (all supplied and pre-encoded on the integrated circuit chip 14 fabricated into the blister pack by the pharmaceutical firm)

pharmacist inserts blister pack 12 or tube 18 into pharmacy reader/writer unit 44;

upon issuing a command, the modified pharmacy computer system software would both print a standard exterior stick-on label and write the doctor-supplied prescription information onto the integrated circuit chip 14 attached to blister pack 12 or tube 18;

pharmacist places the sticky-label on the exterior of the blister pack 12 or tube 18;

pharmacist gives blister pack 14 or tube 18 to user;

user takes bottle home and reads bottle instructions, e.g. take 2 pills 3 times per day on an empty stomach;

user puts package 10 into consumer prompting device 20;

consumer prompting device 20 displays appropriate information about the contents of the package 10, including name of medication and dosage/strength, number of pills (or some other measure of quantity) and frequency, number of repeats allowed, name of user, prescribing doctor, date issued, PLUS warnings and contra-indications, in a scrollable window (contra-indications are also automatically checked against any other medications already 'loaded' into the consumer prompting device 20 when packages are inserted);

warnings indicate factors to be considered before taking the medication: e.g. not to be taken on an empty stomach; do not drive while taking this medication; do not consume alcohol;

user decides to take medication now, so presses TAKE button;

consumer prompting device 20 writes identifying information onto the Integrated circuit chip 14 and generates an entry in the 'next take time table' for that medication . . . the 'next take time' entry is also paired with the encoded range for the take window that was stored on the package 10 (this is used later by the Consumer prompting device 20 when it checks to see if a users choice of a time to take a medication falls within allowed ranges set by the doctor and/or the pharmaceutical manufacturer); Consumer prompting device 20 also writes the 'take time' into the 'take time log' on the integrated circuit chip 14;

consumer prompting device 20 displays message 'REMOVE PACKAGE AND TAKE 2 PILLS' . . . user removes package 10 and takes pills (N.B the user is normally prompted to insert the package 10 AFTER the TAKE button has been depressed, which acts to reinforce the action and validate it or confirm it . . . only in the 'first use' scenario with each new medication is the package 10 already inserted in the consumer prompting device 20 when the user depresses the TAKE button):

the encoded ranges used by the consumer prompting device 20 to calculate the take window in which it will issue directions to the user to take a medication also indicate that this is a 'daytime' medication (i.e. assumes 16 awake hours, 8 sleep hours, so it is not necessary for the user to wake up in the middle of the night to take the next dose) so the consumer prompting device 20 computes and sets the 'next take time' to 5:30 p.m;

at 5:30 p.m. the consumer prompting device 20 beeps or vibrates and displays 'INSERT (medication name)';

user is at a restaurant with a client and does not wish to be disturbed, so he depresses the DEFER button;

consumer prompting device 20 examines the encoded ranges used to calculate take window and computes a DEFER time interval list, displayed as a scrolling list on the Consumer prompting device 20 (e.g. 5, 15, 30 minutes, 1 hour, to maximum as stipulated by pharmaceutical manufacturer);

user anticipates he will be busy for only another 15 minutes, so he scrolls through the list, stops on 15 minutes, and depresses the SELECT button (N.B. DEFER & SELECT are same button);

after 15 minutes, Consumer prompting device 20 beeps or vibrates and displays 'INSERT (medication name)' again;

user inserts package 10 into consumer prompting device 20;

consumer prompting device 20 displays appropriate information about the contents of the package 10, including the name of the medication PLUS warnings and contra-indications, in a scrollable window; p0 consumer prompting device 20 reads warnings and contra-indications from Package 10 and displays them in a scrollable window (e.g. DO NOT TAKE WITH FOOD);

user just ate, so he depresses the DEFER button again, and selects a longer time interval;

consumer prompting device 20 prompts user to remove the package 10;

after the time Interval has elapsed, consumer prompting device 20 again prompts to insert the package 10;

user could either take the medication or continue to defer (if he defers too many times and goes beyond the calculated 'next take time window', the consumer prompting device 20 prompts to insert the package 10 and displays appropriate warnings and corrective actions;

the next day the user wakes at 5:30 a.m. and decides to take his medication prior to the consumer prompting device 20 having prompted him, so he inserts the package 10 into the consumer prompting device 20;

the consumer prompting device 20 computes the take window range for that medication (using the encoded ranges stored with the 'next take time') to see if it is within the acceptable range;

if it is within the acceptable range, consumer prompting device 20 would display 'OK to TAKE';

if it is outside the acceptable range, the consumer prompting device 20 displays 'TOO SOON TO TAKE';

consumer prompting device 20 prompts user to remove the package 10; and and so on.

As discussed above, the hospital version of the medication prompting system of the present invention is an adaptation of the consumer prompting device 20 and package 10 configuration, with variations in hardware, software, and operation, to suit the needs of a hospital setting. The general aim is the same (mechanized control of the delivery of medication), but adapted for a hospital environment. In the case of the consumer prompting device system, the specific aim is to provide a means for a consumer to easily and effectively schedule and log his self-medication regimen, In the case of the hospital system, the aim is to provide a means for hospital staff to schedule, log and monitor the administration of medication to patients, and at the same time provide a higher level of safety and security in the distribution process.

It will be appreciated by those skilled in the art that it is possible to construct a version of this hospital system that is highly interactive with a hospital's own internal online patient database systems. The database systems in widespread hospital use today are produced by a very large number of software vendors, and are custom fitted to a hospital's needs, and consequently are virtually infinite in their variety. However, the same high level functions would be incorporated into each of these systems to implement the system of the present invention. In each case, custom interfaces would be required. The bulk of this interfacing would be centered around avoiding any duplication of effort. Whenever possible, data required by system of the present invention (e.g. patient admission data) would be captured from a hospital's existing database system and passed to the present system. Relevant data from the present system could also be passed back to the hospital's database system.

It is also possible to construct a version of the present system that is for the most part independent of hospital database systems. The following example will therefore be based on this latter version.

For this example, we assume that a hospital floor is divided into nursing stations that are each responsible for a group of rooms. Any number of nurses may be assigned responsibility for these rooms. The following example shows the use of a nurse prompter 162 in a hospital:

patient is admitted to hospital and a Smart Card or Java Ring style identification bracelet is attached to the patient's wrist. The ID bracelet 168 has an integrated circuit chip 170 attached thereto. Information such as the patient's name, date of admission and hospital admission number is written onto chip 170. Preferably in addition patient specific medication allergies and/or any other relevant warnings are also written onto chip 170.

hospital physician(s) prescribe medications and pass these prescriptions to the attending floor nurse, who enters them into the patient's chart or other form of record. Patient medication monitoring in a hospital setting must deal with the complication of passing information between rotating staff. The patient chart, in part, fulfills this obligation.

enter patient information and medications into the nurse prompter-host application running on a workstation 154 in the nurse's station. Entries would include patient's name, room number, hospital id number and admission date . . . entries would also include names of medications and dosage/strength, number of pills (or some other measure of quantity) and frequency, prescribing doctor and date issued, warnings, contra-indications.

order and prepare the medication for each patient in a group of rooms (floor pharmacy nurse)

distribute the medication to each patient (floor dispensing nurse)

floor pharmacy nurse would use the nurse prompter-host at the workstation 154 to obtain a printout or online screen listing of the medications to be ordered for that shift. Medications would be ordered and delivered to the floor pharmacy station as normal.

once the medications have arrived at the floor, they are ready to be loaded into the medication containers 158. Each medication container 158 would have a permanent external marking indicating the room number and bed number (or some other external marking system), in addition to the integrated circuit chip 14 fabricated into the container. The floor pharmacy nurse would select a room number and bed number on the workstation 154. This would display the prescribed medications for the patient, as well as all patient information. The nurse would attached the associated medication container 158 to the Reader/Writer 156 and place medications in the medication container 158. The workstation 154 would write identifying information onto the medication container 158 via the Reader/Writer 156. This process would be completed until all medications for each patient have been loaded (this process is similar to the manual procedures currently practiced in hospital floor pharmacy stations). Medication containers 158 would then be loaded onto a trolley 160 for use by the floor dispensing nurse.

depending on the number of nurses assigned to a group of rooms, the floor dispensing nurse would transfer information via the infra-red port to one or more nurse prompters 162. Based on the frequency information loaded into the nurse prompter at the time the prescription is entered, the nurse prompter generates a 'next take table' for each patient in the nurse prompter 162. Each 'next take table' would contain entries for every medication the patient has been prescribed. Each nurse prompter 162 would contain 'next take tables' similar to those in the consumer prompting device 20.

each floor dispensing nurse would take the nurse prompter 162 associated with her assigned rooms with her on her rounds.

upon arriving at each bedside, the floor dispensing nurse would attach (or swipe) the nurse prompter 162 to the patient's wrist ID bracelet 168. The nurse prompter 162 would open to the identification information it has stored on it for that patient, and display the medication list for that patient The nurse prompter 162 would indicate which medications should be started/administered now, and which ones are not within their take window.

floor dispensing nurse would attach the nurse prompter 162 to the medication container 158 associated with that room & bed. Nurse prompter 162 would verify that it is the correct medication container 158 for that patient by comparing the ID information read from the patient's ID bracelet with the id information stored on the medication container 158. If it is a match, the dispensing nurse would give the medication to the patient and press the MEDICATION DELIVERED field on the screen of the nurse prompter 162 with a stylus pen. The nurse prompter 162 would log the data and time the medication was administered. This process would be repeated for each medication displayed on the nurse prompter 162.

floor dispensing nurse would repeat this process with each patient in the group of rooms associated with the nurse prompter 162.

the nurse prompter 162 would also continuously scan the 'next take table' for each medication of each patient, looking for alerts to be triggered. If a medication has not been administered in time, the nurse prompter would alert the floor dispensing nurse (vibration, followed by a blinking screen, followed by an audible alarm).

when an alert is triggered (a match between current date and time), the nurse prompter 162 would display a container number, and the patient's name and medication list, and prompt the nurse to administer the medication. The dispensing nurse could either press DEFER on the Nurse prompter screen, or DELIVER and then proceed to the patient's bedside. The nurse prompter 162 would at this point be waiting for the nurse to confirm that she has the right patient by attaching (or swiping) the nurse prompter to the patient's wrist ID bracelet. If it is the correct patient, the nurse prompter 162 would prompt the nurse to attach the associated medication container 158. If the correct medication container 158 is attached, the nurse prompter would prompt to administer the medication and write log data to the nurse prompter the workstation 154 would act as a 'supervisor' of the Nurse prompters:

if new medications are issued for a patient, the workstation 154 would prompt for the connection of the correct nurse prompter 162 to update its 'next lake table'.

the workstation 154 would periodically prompt for the connection of each nurse prompter 162 so that maintenance tasks could be performed (e.g. backing up data from the nurse prompter).

nurse prompter 162 could display a color image of the medication to be administered, as a cross check for accuracy (e.g. an image of the pill showing the distinctive shape, color and markings on the pill).

in the case of liquid medications, single use medication container cups with integrated circuit chip 14 attached thereto could be used.

The system can be further modified by providing an integrated circuit chip in the packages that contain bulk medication. Thereby the pharmaceutical company can update the information with regard to the medication and disseminate it The pharmacy can then copy the information from the pharmaceutical company directly from the integrated circuit chip into the pharmacy computer system and transfer it to the integrated circuit chip 14 attached to the dispensing package. This is particularly useful where the pharmaceutical company has identified new contra-indicators or hazards.

Preferably the software that is used to implement the above described system con be used on a wide variety of operating systems and platforms. A Java™ based system would be portable and adaptable to pharmaceutical systems and hospital systems made by a number of manufacturers.

It will be appreciated by those skilled in the art that the consumer prompting system of the present invention may be used as a single purpose system. For example it could be adapted for use for use in association with the birth control pill. Since in this example only one medication is being monitored the systems can be greatly simplified. Alternatively the consumer prompting device of the present invention could be used as a multi-person prompting system for example, for a family. In this embodiment the reminder notification would identify not only the medication but also the user. The different users could also be identified with a different sound. Each user could have a personal integrated circuit chip for their own use so that not only the medication could be verified but also the user.

There are a number of advantages of the present invention over the prior. For example since the information with regard to the method of calculating the next take time, best practices, contra indicators, hazards and the like is stored on the individual medication packages the consumer prompter device 20 can manage a large number of medication because the only information that is required to be stored on device 20 is the name of the medication and the next take time. Accordingly, the memory requirements for each medication are relatively low. Further, the cost of attaching an integrated circuit chip to a package is relatively low and since no power source is required in association with the package 10 (only device 20), the cost of operating the prompting and monitoring system of the present Invention is relatively low. Since the integrated circuit chip 14 is non-volatile it need not be attached to device 20 to store information and thus device 20 can readily be used with multiple medications. The present invention provides a simple and user friendly method of a patient monitoring the correct use of their medication. The present invention provides a method of prompting the consumer to take a medication and then verifying that it is the correct medication before the consumer takes the particular medication. As discussed above, after the consumer prompting device 20 prompts the consumer to take a medication, the integrated circuit chip 14 identified as being associated with the particular medication must be read by the read/write module so as to confirm that the correct medication was taken. Thus the consumer prompting device provides a method of verifying that the correct medication was taken.

A further advantage of the present system is that the times at which the medication is actually taken is stored on the integrate circuit chip 14 thus the physician or other health care professional can monitor the actual use of the medication. This information can be invaluable when considering altering the dosage or use of the medication. Further, this information will be useful for medical and pharmaceutical research and in some instances for the patient's health insurance.

It will be appreciated that the above description related to the invention by way of example only. Many variations on the invention will be obvious to those skilled in the art and such obvious variations are within the scope of the invention as described herein whether or not expressly described.

What is claimed as the invention is:

1. An interactive reminder device for use in association with a packages having an integrated circuit chip attached thereto comprising:

a read/write module adapted to read information stored on an identifiable integrated circuit chip and to write information onto the identifiable integrated circuit chip attached to a package;

a means for confirming the identifiable integrated circuit chip is read from and written to by the read/write module;

an integrated circuit operably connected to the read/write module;

a power supply operably connected to the integrated circuit memory operably connected to the integrated circuit;

a clock operably connected to the integrated circuit, and a prompting means operably connected to the integrated circuit.

2. An interactive reminder device as claimed in claim 1 further including a screen operably connected to the read/write module for displaying information thereon.

3. An interactive reminder device as claimed in claim 2 further including a plurality of buttons operably connected to the integrated circuit and to the screen adapted to scroll through and select information displayed on the screen.

4. An interactive reminder device as claimed in claim 1 further including a means for confirming the identifiable integrated circuit chip is read from and written to by the read/write module.

5. An interactive reminder device as claimed in claim 1 wherein the prompting means is chosen from the group consisting of a beep, a vibration and a visual indicator.

6. An interactive reminder device as claimed in claim 5 including a combination of prompting means.

7. An interactive reminder device as claimed in claim 1 wherein the device is incorporated in an electronic personal organiser.

8. A method for prompting for the use of medication using a unique identifier comprising the steps of:

reading information stored on an integrated circuit chip regarding a method of calculating a next take time, determining if an identifier field on the integrated circuit chip is empty and if empty, writing the unique identifier onto the integrated circuit chip, if not empty, determining if the identifier in the identifier field is not the unique identifier then exiting and if the unique identifier is thereafter present in the identifier field:

calculating the next take time;

storing a next take time in a prompting device;

prompting at the next take time.

9. A method for prompting for the use of medication as claimed in claim 8 further including the steps of identifying an identifiable integrated circuit chip associated with the stored next take time and confirming the identifiable integrated circuit chip is associated with the prompted next take time.

10. A method for prompting for the use of medication as claimed in claim 9 wherein a name of the medication associated with the integrated circuit chip is stored in association with the next take time and the name is displayed on the prompting device at the next take time.

11. A method for prompting for the use of medication as claimed in claim 10 further including the steps of identifying that the medication is taken and writing the take time onto the integrated circuit chip.

12. A method for prompting for the use of medication as claimed in claim 11 further including the step of displaying the information stored on the integrated circuit chip on the prompting device.

13. A method for prompting for the use of medication as claimed in claim 12 further including the steps of calculating a next take window and identifying if the present time is within the next take window.

14. A method for prompting for the use of medication as claimed in claim 13 further including the steps of calculating a deferred next take time and prompting at the deferred next take time.

15. A method for monitoring the use of medication in a health care facility comprising the steps of:

calculating the next take time for an identifiable patient for an identifiable medication;

storing a next take time, the identified medication and the identified patient in a prompting device;

prompting at the next take time;

confirming that the medication integrated circuit chip is the medication integrated circuit chip associated with the identified medication; and confirming that the patient integrated circuit chip is the patient integrated circuit chip associated with the identified patient and thereafter administering the identified medication to the identified patient.

16. A method for monitoring the use of medication in a health care facility as claimed in claim 15 further including the step of writing the take time and the medication onto the patient integrated circuit chip.

17. A method for monitoring the use of medication in a health care facility as claimed in claim 16 further including the step of writing the take time and the medication onto a prompting device.

18. A method for monitoring the use of medication in a health care facility as claimed in claim 15 further including the steps of calculating a deferred next take time and prompting at the deferred next take time.

19. A method for monitoring the use of medication in a health care facility as claimed in claim 15 wherein the patient integrated circuit chip is attached to the patient identification bracelet.

20. A package for tracking information for use in association with a reader/wrter comprising;

a package;

an integrated circuit chip integrally attached to the package for storing information regarding contents of the package and periodically receiving new information with regard to the use of the package whereby removing the integrated circuit chip from the package would destroy the package.

21. A package as claimed in claim 20 wherein the package is a plastic medicine bottle.

22. A package as claimed in claim 20 wherein the package is a blister pack.

23. A package as claimed in claim 20 wherein the package is a tube.

24. A package as claimed in claim 20 wherein the integrated circuit chip has an antenna operably attached thereto.

* * * * *